US010195416B2

United States Patent
Gebauer et al.

(10) Patent No.: US 10,195,416 B2
(45) Date of Patent: Feb. 5, 2019

(54) APPARATUS AND METHOD FOR MAKING A STERILE CONNECTION OF FLEXIBLE TUBING

(71) Applicant: GE Healthcare Bio-Sciences AB, Uppsala (SE)

(72) Inventors: Klaus Gebauer, Uppsala (SE); Eric Faldt, Uppsala (SE); Nachiket Karmarkar, Bangalore (IN)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 270 days.

(21) Appl. No.: 14/892,649

(22) PCT Filed: May 19, 2014

(86) PCT No.: PCT/SE2014/050609
§ 371 (c)(1),
(2) Date: Nov. 20, 2015

(87) PCT Pub. No.: WO2014/189446
PCT Pub. Date: Nov. 27, 2014

(65) Prior Publication Data
US 2016/0082245 A1    Mar. 24, 2016

(30) Foreign Application Priority Data

May 20, 2013    (IN) .......................... 1496/DEL/2013

(51) Int. Cl.
*A61M 39/18*    (2006.01)
*F16L 33/30*    (2006.01)

(52) U.S. Cl.
CPC ......... *A61M 39/18* (2013.01); *A61M 2207/00* (2013.01); *F16L 33/30* (2013.01); *F16L 2201/44* (2013.01)

(58) Field of Classification Search
CPC .... A61M 39/12; A61M 39/162; A61M 39/16; A61M 2207/00; A61M 39/18; F16L 2201/44; F16L 33/30
See application file for complete search history.

(56) References Cited

U.S. PATENT DOCUMENTS 4,443,215 A  *  4/1984  Smith ................. A61M 39/143
                                                     141/1
4,619,642 A  *  10/1986  Spencer ............. A61M 39/146
                                                     604/29
(Continued)

FOREIGN PATENT DOCUMENTS

DE    102007032771 A1    1/2009
EP        0107271 A1    5/1984
(Continued)

OTHER PUBLICATIONS

International Search Report and Written Opinion issued in connection with corresponding PCT Application No. PCT/SE2014/050609 dated Oct. 9, 2014.
(Continued)

*Primary Examiner* — Theodore Stigell
*Assistant Examiner* — Hazma Darb
(74) *Attorney, Agent, or Firm* — Wood IP LLC (57) ABSTRACT

An apparatus for substantially sterile connection of flexible tubing, including at least one tubing holder, which is adapted to receive one or more lengths of flexible tubing and which is also equipped with one or more steriliant applicators. The steriliant applicator is adapted to apply a steriliant to the length of tubing when the tubing length is received in the tubing holder. At least one cutter, which is movable in relation to the tubing holder and adapted to cut the length of tubing. A connector holder, which includes a compartment housing and a substantially sterile tubing connector. The connector holder is movable in relation to the tubing holder
(Continued)

to a position where the length of tubing and the sterile tubing connector are aligned and can be urged together.

18 Claims, 10 Drawing Sheets

(56) References Cited

U.S. PATENT DOCUMENTS

| | | | |
|---|---|---|---|
| 5,743,892 | A | 4/1998 | Loh et al. |
| 5,965,086 | A | 10/1999 | Rose et al. |
| 6,485,593 | B1 | 11/2002 | Christoffersen |
| 6,524,304 | B1 | 2/2003 | Picou et al. |
| 6,679,529 | B2 | 1/2004 | Johnson et al. |
| 7,540,681 | B2 | 6/2009 | Cybulski et al. |
| 2008/0265561 | A1* | 10/2008 | Buchanan ............ A61M 39/18 285/21.1 |
| 2013/0273594 | A1* | 10/2013 | Ahimou ................ A61L 2/28 435/31 |

FOREIGN PATENT DOCUMENTS

| | | |
|---|---|---|
| EP | 0507321 A1 | 10/1992 |
| EP | 0643975 A1 | 3/1995 |
| EP | 1547755 A1 | 6/2005 |
| JP | 59022556 A | 2/1984 |
| JP | 04308731 A | 10/1992 |
| JP | H07329182 A | 12/1995 |
| JP | 11506378 A | 6/1999 |
| JP | 2001187135 A | 7/2001 |
| JP | 2008515484 A | 5/2008 |
| WO | 199408173 A1 | 4/1994 |
| WO | 9735634 A1 | 10/1997 |
| WO | 02066098 A1 | 8/2002 |
| WO | 2008005882 A2 | 1/2008 |

OTHER PUBLICATIONS

European Search Report from EP Appl. No. 14 80 1447, dated Dec. 9, 2016.
Japan Notice of Preliminary Rejection for Japanese Patent Application No. 2016-515314, dated Mar. 27, 2018, 4 pages.

* cited by examiner

APPARATUS AND METHOD FOR MAKING A STERILE CONNECTION OF FLEXIBLE TUBING

CROSS-REFERENCE TO RELATED APPLICATIONS

This application is a national stage application under 35 U.S.C. § 371(c) of prior filed, co-pending PCT application serial number PCT/SE2014/050609, filed on May 19, 2014, which claims priority to Indian Patent Application Serial No. 1496/DEL/2013, titled "ASEPTIC CONNECTOR" filed May 20, 2013. The above-listed applications are herein incorporated by reference.

BACKGROUND OF THE INVENTION

Technical Field of the Invention

Embodiments of the invention relate to connection of flexible tubing, and more particularly to an apparatus for substantially sterile connection of flexible tubing. The invention also relates to a method for substantially sterile connection of sterile tubing.

Description of the Related Art

Single use systems, also called disposable systems, are more and more used in the bioprocess industry. For example, separation or reaction systems such as chromatography systems, filter systems, or bioreactor systems have today at least partly been provided as disposable systems. This eliminates the need for cleaning and cleaning validation before processing, in between processes and cycles, or after processing before re-use as required for conventional re-usable equipment. With disposable systems, cross-contamination is avoided. Bioburden control of single-use equipment during manufacturing of the equipment itself is required to eliminate cleaning needs before bringing single-use equipment into product contact. This is usually achieved by manufacturing of single-use equipment in controlled environment (clean room), often followed by sterilisation processes (gamma irradiation). The demands of the level of bioburden control can differ for different applications, however, bioburden control to a certain degree of the equipment is not only required for some applications, but also considered as the preferable option for most of the applications using disposable equipment. The production of this equipment in controlled environments is required to guarantee a low initial level of contaminants prior to the bioburden control procedure, hereby reducing for example endotoxin levels.

Typical applications of aseptic connectors in biomanufacturing are connections between fluid lines, separation units (filters, chromatography columns, adsorbers, membrane adsorbers, expanded or fluidized bed adsorbers), or reaction units (bioreactors, reaction or (bio-) conversion units that for example utilize enzymatic conversions).

Sterility and asepsis are terms used to define the state of a system, a piece of equipment, or a fluid conduit as being in control of bioburden levels to different degrees. Aseptic connectors can be used to interconnect single-use equipment and also single-use equipment and conventional re-use equipment that is bioburden controlled (sanitized, sterilized etc.). Available aseptic connectors are for example Ready-Mate™ connectors from GE Healthcare and Kleenpack™ from Pall. These use removable protective films to ensure asepsis and are applied to lengths of tubing and/or equipment in a manufacturing operation, after which the tubing/equipment with the connectors is gamma sterilized. This means that they are only useful for preassembled circuits.

For assembly of tailor-made aseptic circuits directly at the place of use, the current approach is to use heat welding of flexible tubing. Welders for this purpose use electrically heated wafers to cut and weld tubing, and are commercially available from, e.g., GE Healthcare (Sterile Tube Fuser) and Sartorius Stedim Biotech (BioWelder™). The aforementioned equipment are stationary, heavy, and require electrical connection.

Accordingly, there is a need for lighter and more convenient devices to be used in aseptic connection of flexible tubing in, e.g., bioprocessing settings.

SUMMARY OF THE INVENTION

In an embodiment, an apparatus for substantially sterile connection of flexible tubing includes at least one tubing holder, which is adapted to receive one or more lengths of tubing and equipped with one or more sterilant applicators that are adapted to apply a sterilant to the one or more lengths of tubing upon reception of the one or more lengths of tubing in the at least one tubing holder. The apparatus further includes at least one cutter, which is movable in relation to the at least one tubing holder and adapted to cut the one or more lengths of tubing. The apparatus further includes a connector holder that includes a compartment, which houses a substantially sterile tubing connector. The connector holder is movable in relation to the at least one tubing holder to a position where the one or more lengths of tubing that are cut and the sterile tubing connector are aligned and can be urged together. According to aspects, such an apparatus is small, has a low weight, does not require electrical connection, and/or is generally convenient to use.

In an embodiment, the apparatus can be handheld and used to connect tubing in situ, even in inconvenient locations which are not possible to access with heavy electrical welding equipment. In another embodiment, non-weldable tubing may be connected, e.g. rubber tubing.

Another aspect of the invention is to provide a simple and convenient method for substantially sterile connection of flexible tubing directly in a bioprocess setting.

BRIEF DESCRIPTION OF THE DRAWINGS

FIGS. 1A, 1B, 1C, 1D and 1E show an apparatus of the invention through the different steps of the method of the invention.

FIGS. 3A, 3B, 3C, 3D and 3E show alternative embodiments of the apparatus of the invention and its use.

FIGS. 4A and 4B show further embodiments of the apparatus, with different types of connectors. FIG. 4B shows a T-connector.

FIGS. 7A and 7B show a rotary embodiment of the apparatus of the invention.

DETAILED DESCRIPTION

One embodiment of the invention includes an apparatus 1;11;61 for substantially sterile connection of flexible tubing, as illustrated by FIGS. 1A through 1E, FIG. 2, FIGS. 3A through 3E, FIGS. 4A and 4B, and FIGS. 7A and 7B.

In an embodiment, an apparatus comprises at least one tubing holder 2;12;62, which is adapted to receive one or more lengths of flexible tubing 3;13;63 and which is also equipped with one or more sterilant applicators 4;14;64. The sterilant applicator(s) is/are adapted to apply a sterilant to one or more lengths of tubing 3;13;63 when the tubing length(s) is/are received in the tubing holder 2;12;62. The tubing holder(s) may each comprise an essentially cylindrical port of a diameter suitable to receive a length of tubing and the port may, e.g., lead into a tubing end receiver located in a connector holder 6 or into a cutting and connecting compartment 19. The port(s) can suitably be covered with protective film(s) or cap(s), to be removed before receiving the length(s) of tubing. The sterilant applicator(s) may, e.g., each be a tubular or slit tubular layer of a flexible open-porous material (e.g., a polymer foam) arranged on the inner surface of the cylindrical port(s). The sterilant applicator(s) may contain an imbibed liquid sterilant, such as hydrogen peroxide or an aqueous hydrogen peroxide solution, e.g., comprising 3-60 wt. % or 25-35 wt % hydrogen peroxide.

Figure 2:
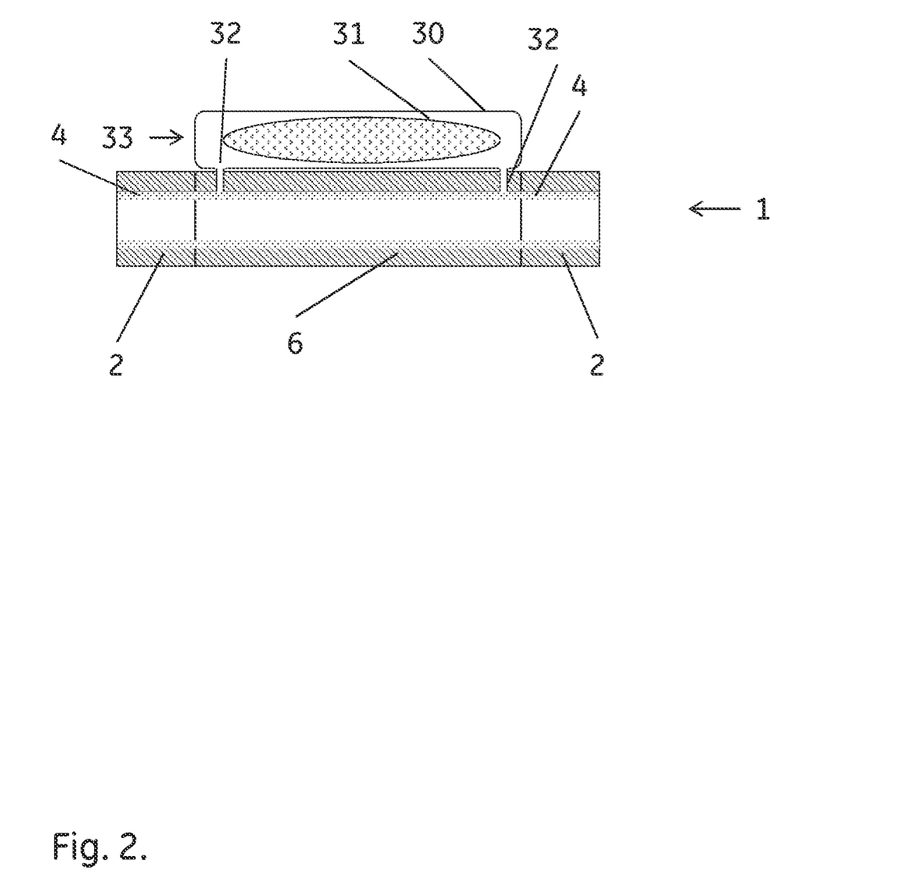
FIG. 2 shows an embodiment of the apparatus of the invention with a sterilant reservoir.
Figure 3A:
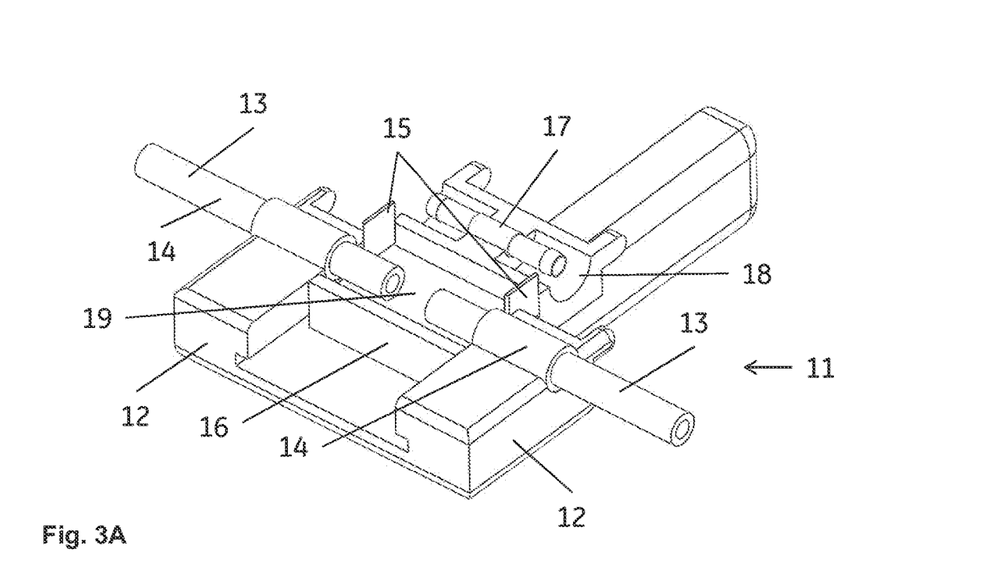
FIG. 3A shows the apparatus with two lengths of tubing inserted.
Figure 3B:
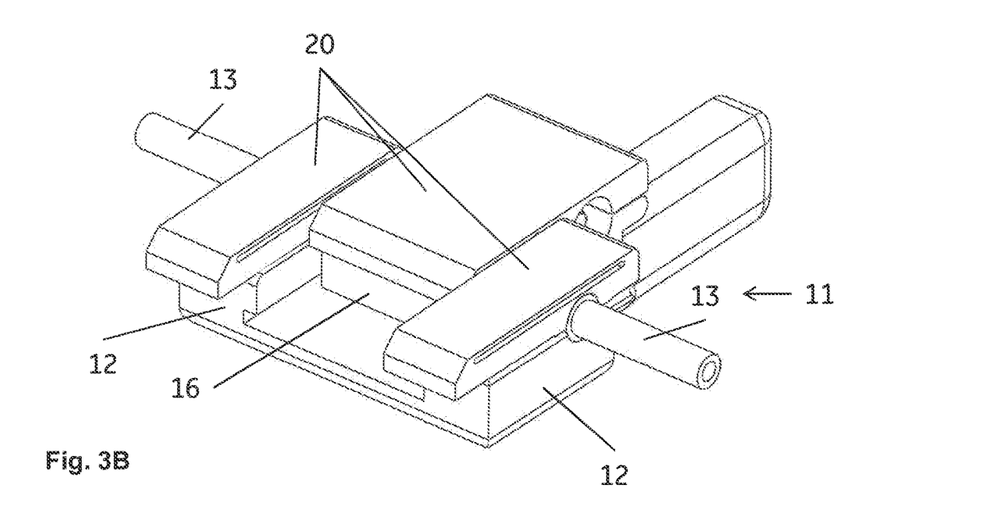
FIG. 3B shows the apparatus after the cut lengths of tubing and the connector have been urged together.
Figure 3C:
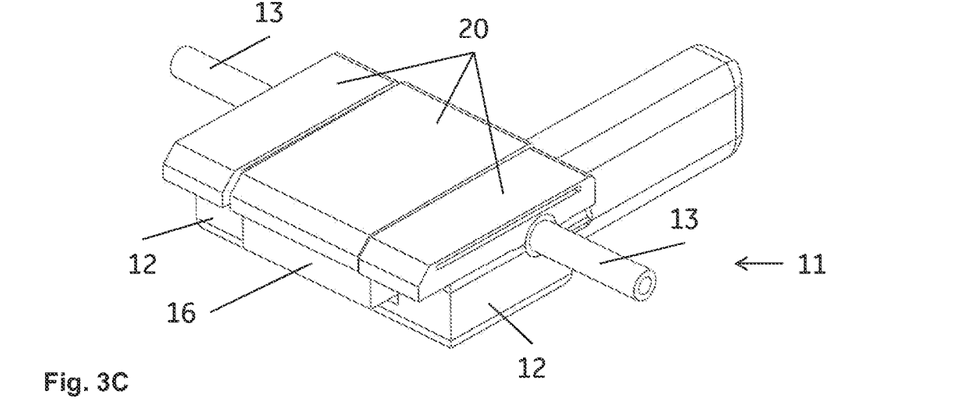
Figure 3D:
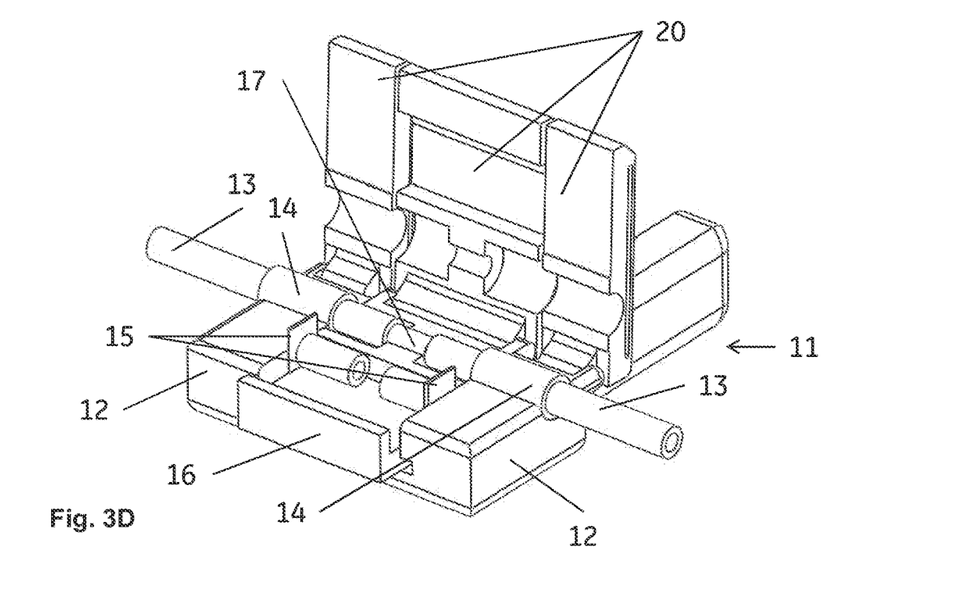
Figure 3E:
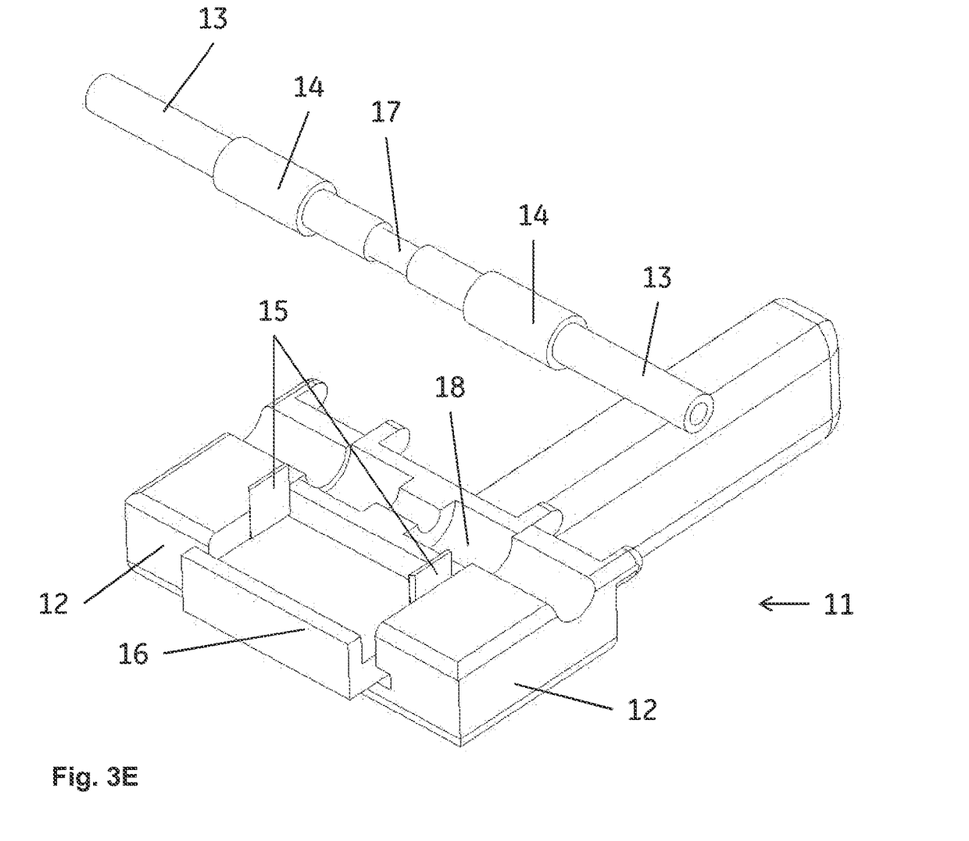

In an embodiment, the sterilant applicator(s) may also, or alternatively, be fluidically connected or fluidically connectable to a sterilant reservoir 33 comprising a liquid sterilant, such as hydrogen peroxide or an aqueous hydrogen peroxide solution, e.g., comprising 3-60 wt. % or 25-35 wt % hydrogen peroxide. In both cases, the sterilant can alternatively also be a solution comprising ethanol (typically a 60-80 wt % aqueous ethanol solution), hypochlorite (typically a 0.5-10 wt % aqueous sodium hypochlorite solution), etc. The use of hydrogen peroxide solutions has the advantage that any residues of hydrogen peroxide will react to form non-toxic water and oxygen. Aqueous hydrogen peroxide solutions possess germicidal properties over a concentration interval from below 1 wt % to 95-100 wt %, but the effect is more reliable and rapid at concentrations of 10 wt % and higher. Hydrogen peroxide at high concentrations may pose an explosion hazard, so 10-60 wt % or in particular 25-35 wt % is the concentration in an embodiment.

In an embodiment, the apparatus includes at least one cutter 5;15;65, which is movable in relation to the tubing holder 2;12;62 and adapted to cut the length(s) of tubing 3;13;63. The cutter(s) can be a blade or a similar device with a sharp edge, e.g., a sharp edge on a tubing holder, or it can alternatively be a heated wafer or even, e.g., a laser. The cutter(s) can be movable in a direction essentially transverse to the length(s) of tubing received in the tubing holder(s). The cutter (or each cutter) may be movable in a plane interfacing a tubing holder and a connector holder, or a cutting and connecting compartment, in a direction towards the length of tubing received in the tubing holder. The cutter(s) can be movable independently or together with the connector holder.

In an embodiment, the apparatus includes a connector holder 6;16;66, which includes a compartment 8;18;68 housing a substantially sterile tubing connector 7;17;67. The connector holder is movable in relation to the tubing holder 2;12;62 to a position where each cut length of tubing 3;13;63 and the sterile tubing connector 7;17;67 are aligned and can be urged together. The compartment suitably extends in a direction essentially parallel to the tubing port(s) and to the length(s) of tubing received in the tubing holder(s).

In some embodiments, the apparatus also comprises a sterilant reservoir 33, adapted to supply sterilant to the sterilant applicator(s) 4;14;64, such as each sterilant applicator. The sterilant reservoir may, e.g., comprise a breakable ampoule 31 containing a sterilant. Such a breakable ampoule may, e.g., be contained in an ampoule compartment 30, which is fluidically connected to the sterilant applicator(s) via fine tubing or conduits 32 inside one or more of the tubing holder(s) and/or the connector holder. When the ampoule is broken, the sterilant will partially fill the ampoule compartment and flow towards the sterilant applicator(s) by, e.g., gravity or capillary suction, filling or partially filling the sterilant applicator(s) with sterilant. The sterilant reservoir 33 may also be integrated with the sterilant applicator(s) 4;14;64. It is, e.g., possible to use one or more sterilant applicators pre-filled with sterilant and covered with, e.g., a protective film which may be removed before insertion of the tubing length(s). Such a protective film or cap may, e.g., be integrated with a protective film or cap covering a port, as described above. The sterilant comprised in the breakable ampoule or in the pre-filled sterilant applicator(s) may as described above be, e.g., an aqueous solution comprising hydrogen peroxide, e.g., a solution comprising 3-60 wt % or 25-35 wt % hydrogen peroxide.

Figure 1A:
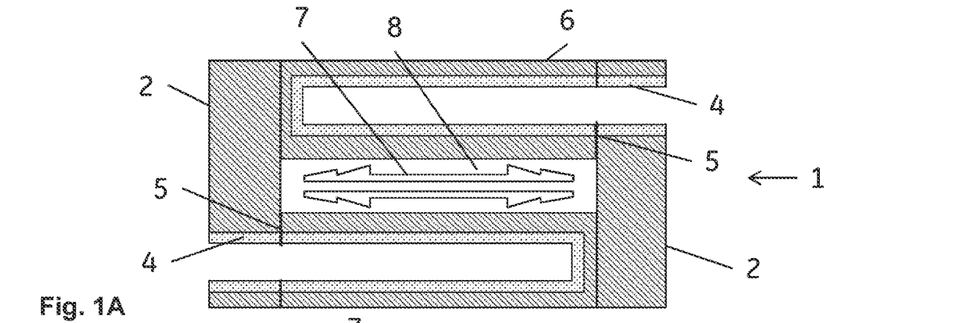
FIG. 1A shows the apparatus before use.
Figure 1B:
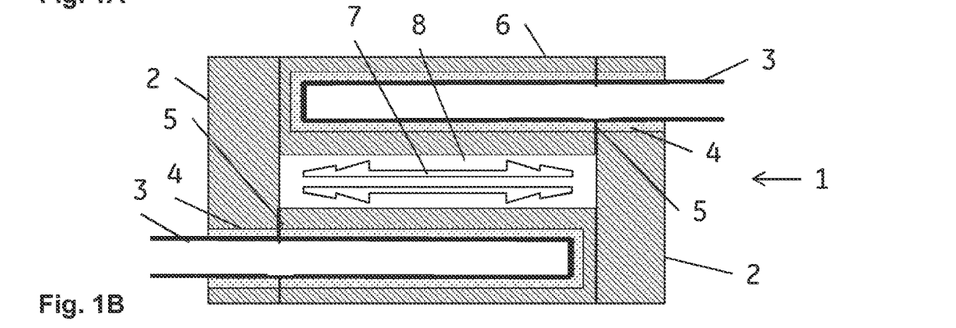
FIG. 1B shows the apparatus with two lengths of tubing inserted.
Figure 1C:
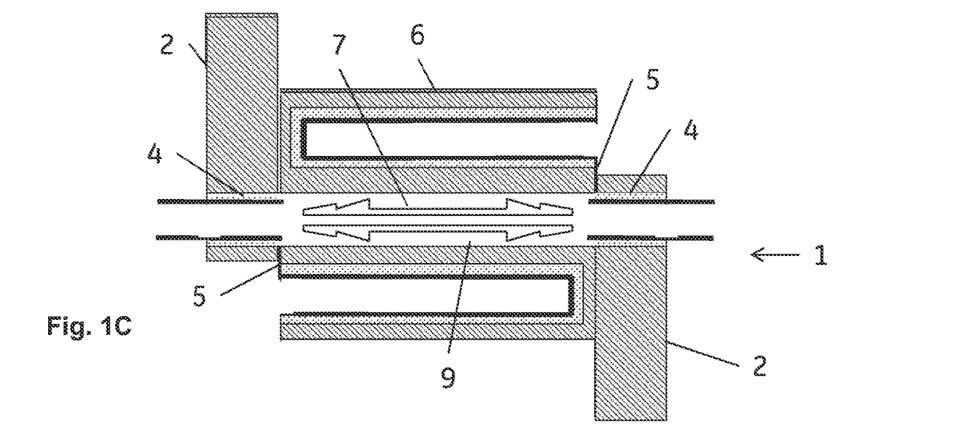
FIG. 1C shows the apparatus after cutting the lengths of tubing and alignment of the tubing lengths with the connector.
Figure 1D:
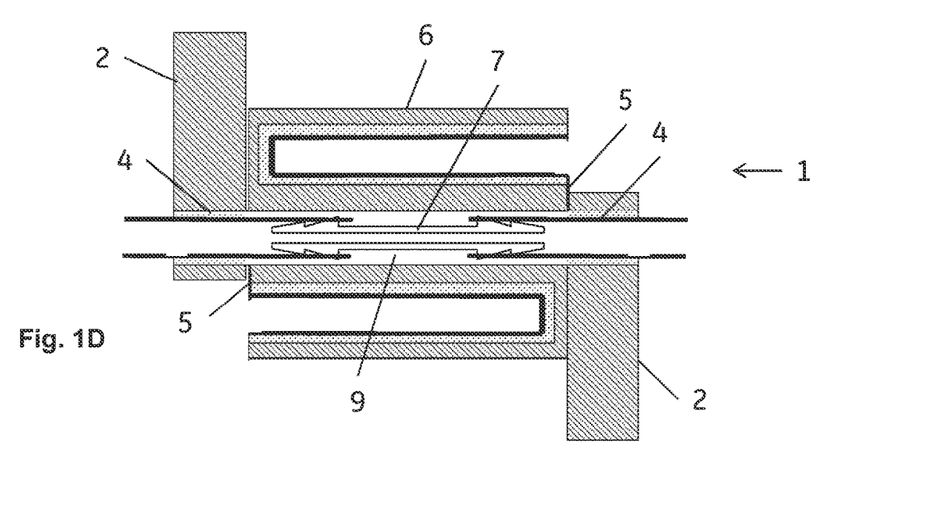
FIG. 1D shows the apparatus after the cut lengths of tubing and the connector have been urged together.
Figure 1E:
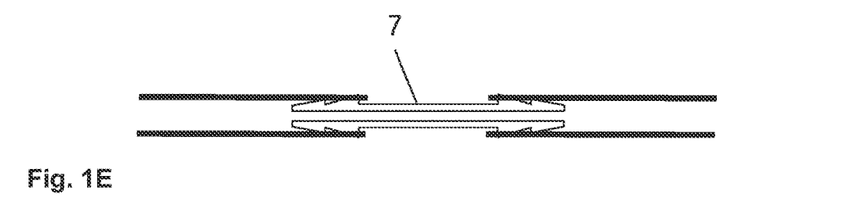
FIG. 1E shows the removed tubing/connector assembly.

In certain embodiments, the apparatus further comprises a movable cover 20 (not shown in FIG. 1), which in a closed position delimits a cutting and connecting compartment 9; 19 and in an open position allows removal of the cut and connected length(s) of tubing. The device can, e.g., be supplied with the cover in a closed position and presterilized by, e.g., gamma irradiation, such that the cutting and connecting compartment is substantially sterile. After cutting the tubing length(s) and urging together with the connector, the cover may then be opened to allow the removal. The cover may be temporarily locked in the closed position by a removable seal or tape, etc. to prevent premature opening of the cover. The movable cover 20 may be one integral cover or it may be divided into a plurality of part covers.

The apparatus 1;11;61 may be adapted for either linear or rotary movement of the connector holder 6;16;66 and cutter(s) 5;15;65 in relation to the tubing holder(s) 2;12;62. Linear versions are illustrated in FIGS. 1A-4B and a rotary version in FIGS. 7A-7B. Advantages of the rotary version are that the cutters 65 may be easier to keep sterile and that a compact design can be achieved.

Figure 4A:
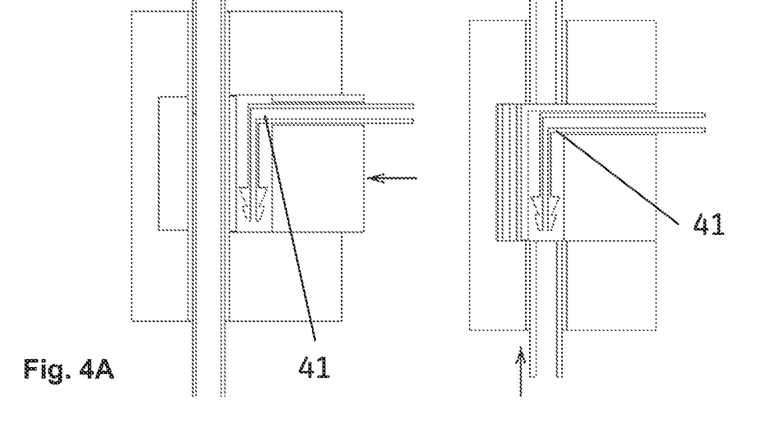
FIG. 4A shows a-way angled hose-barb connector.
Figure 4B:
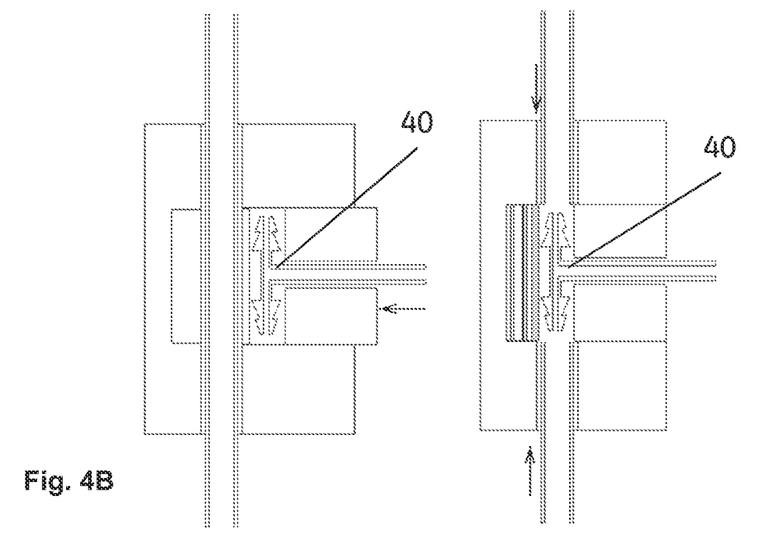

In some embodiments, the tubing connector 7;17;67 is a hose barb connector. The tubing connector can further be, e.g., a straight two-way connector 7;17;67, a three-way T-connector 40, or an angled connector, such as an angled two-way connector 41, as illustrated in FIGS. 4A and 4B.

Figure 5A:
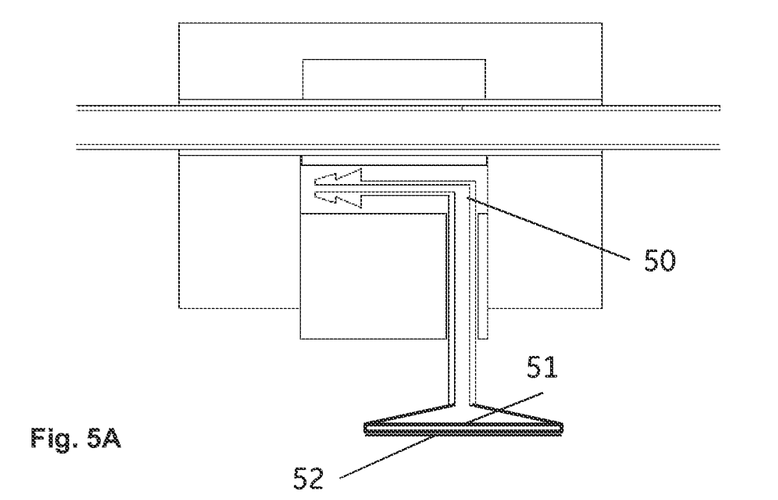
FIGS. 5A and 5B show an embodiment comprising a connector with a removable protective film/cap.
Figure 5B:
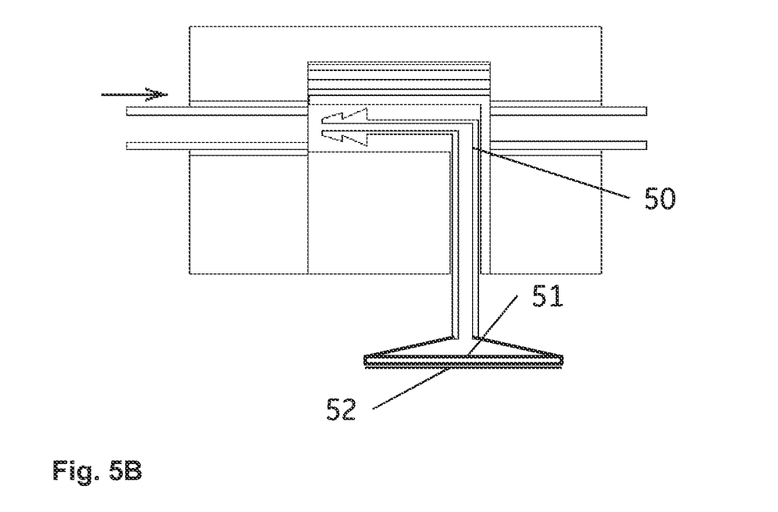

In certain embodiments, illustrated by FIGS. 5A and 5B, the tubing connector 50 comprises a port 51 covered with a removable protective film or cap 52. Suitable such ports are described in, e.g., U.S. Pat. No. 6,679,529 and WO1994008173A1, which are hereby incorporated by reference in their entirety. The removable film or cap ensures that the connector with the attached tubing length(s) is substantially sterile and it can later be connected aseptically to another port with removable film or cap without having to use a laminar flow bench or similar.

In some embodiments, the tubing holder is adapted to receive a length of tubing at a point distant from the ends of the length of tubing. In this case the tubing holder may comprise a recess arranged to receive a portion of the length of tubing and a movable cover (either separate or forming a part of movable cover 20) arranged to be movable from an open position to a closed position where it covers the recess with the tubing portion. One or more sterilant applicators is/are arranged to apply sterilant to the tubing portion, such as over the entire tubing portion received in the tubing holder. The sterilant applicator(s) can, e.g., be wrapped around the tubing portion or may comprise one layer on the recess and one on the inside of the movable cover, such that when the movable cover is in a closed position, the tubing portion is essentially completely surrounded by the sterilant applicators. An advantage of receiving a length of tubing without receiving the ends of the length is that the apparatus can be used to disconnect a length of tubing already attached in both ends. For this purpose, the apparatus can suitably comprise two sterile tubing connectors, of which one or both can be blind connectors and/or one or both can be tubing connectors comprising a port covered with a removable protective film or cap as described above and in FIGS. 5A and 5B. It is of course also possible to use a three-way tubing connector as illustrated in FIG. 4B in order to connect a further length of tubing. When the length of tubing is filled with liquid, in an embodiment, it is drained before disconnection.

Figure 6:
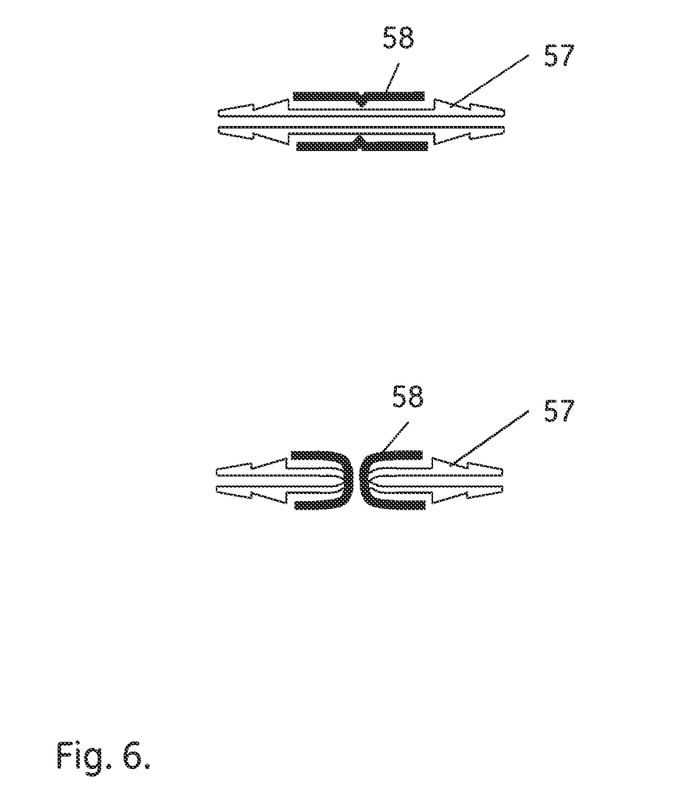
FIG. 6 shows an embodiment where the connector comprises a notched metal tube.
Figure 7A:
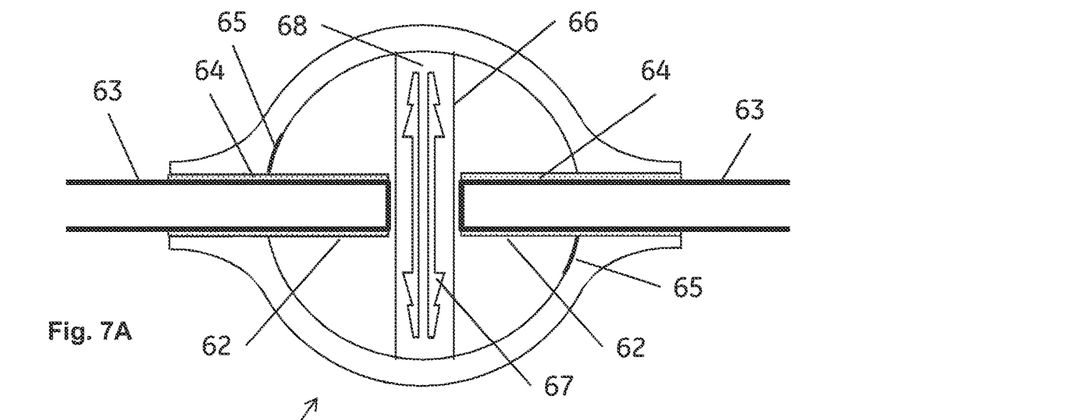
FIG. 7A shows the apparatus with two lengths of tubing inserted.
Figure 7B:
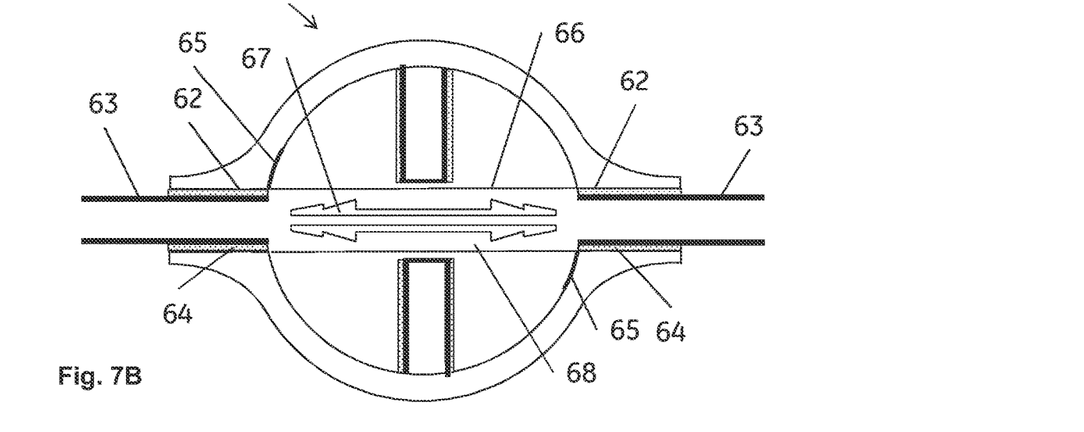
FIG. 7B shows the apparatus after cutting the lengths of tubing and aligning the tubing lengths with the connector.

In some embodiments, illustrated by FIG. 6, the tubing connector 57 is prepared from a deformable plastic and a central part of the tubing connector is concentrically contained in a notched metal tube 58 adapted to upon external compression cut off the tubing connector and fluidically seal off the cut tubing connector ends. At the place of the notch, the inside of the metal tube may have a sharp transverse edge, which upon compression with, e.g., a pair of pliers, can cut the plastic of the connector. Upon a slight bending of the compressed assembly, the connector can be cut off, leaving the ends sealed by the compressed metal tube ends. This allows for convenient aseptic disconnection once the tubing connection is no longer needed. The metal tube can suitably be made from an easily deformable metal such as, e.g., aluminum. The deformable plastic may, e.g., be a polyolefin such as polypropylene or polyethylene.

In certain embodiments, each cutter 5;15;65 comprises a blade or a sharp edge of the connector holder 2;12;62.

In some embodiments, the apparatus has been sterilized, optionally using ionizing radiation.

One embodiment of the invention discloses a method for substantially sterile connection of flexible tubing, comprising the steps of: providing the apparatus of the embodiments described above and at least one length 3;13;63 of flexible tubing; placing the (or each) length of tubing in the (or each) tubing holder 2;12;62 and applying sterilant to the tubing with the (or each) sterilant applicator 4;14;64; moving the cutter or cutters 5;15;65 to cut the (or each) length of tubing; moving the connector holder 6;16;66 to the position where the connector 7;17;67 is aligned with the (or each) cut length of tubing; urging the connector and the (or each) cut length of tubing together to form a connected assembly; and removing the connected assembly from the apparatus.

The movements in moving the cutter or cutters 5;15;65 to cut each length of tubing; and moving the connector holder 6;16;66 to the position where the connector 7;17;67 is aligned with each cut length of tubing; may be linear or rotational, and the position in moving the connector holder 6;16;66 to the position where the connector 7;17;67 is aligned with the cut length of tubing, which may be a linear position or an angular position. The flexible tubing can be flexible plastic tubing (e.g., plasticised PVC) or flexible elastomeric tubing (e.g., thermoelastomer tubing or rubber tubing, including silicone rubber). The tubing can suitably be flexible enough to allow manual cutting with a blade and is suitably free from metal reinforcements. The wall thickness of the tubing may, e.g., be 0.5-5 mm, such as 1-3 mm, and the inner diameter of the tubing may, e.g., be 1-20 mm, such as 2-10 mm.

The length(s) of tubing 3;13;63 may be sealed at both ends and presterilized, e.g., by exposure to gamma irradiation. The sealed ends may have circular cross sections to allow for easy introduction in circular cylindrical ports.

In certain embodiments the method further comprises, before placing each length of tubing in each tubing holder 2;12;62 and applying sterilant to the tubing with each sterilant applicator 4;14;64, a step of fluidically connecting the sterilant in the sterilant reservoir 33 with the (or each) sterilant applicator 4;14;64. If the sterilant reservoir comprises a breakable ampoule 31 with sterilant (e.g., an aqueous hydrogen peroxide solution), this step may comprise the breakage of the breakable ampoule.

In some embodiments the method further comprises a step of breaking an ampoule 31 containing the sterilant.

In certain embodiments, the method further comprises a step of opening a cover 20 between the steps of urging the connector and each cut length of tubing together to form a connected assembly; and removing the connected assembly from the apparatus.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An apparatus for substantially sterile connection of flexible tubing in a non-heating process, comprising:
    at least one tubing holder, adapted to receive one or more lengths of said tubing and equipped with one or more sterilant applicators adapted to apply a sterilant to the one or more lengths of tubing upon reception of the one or more lengths of tubing in the at least one tubing holder;
    at least one cutter, movable in a direction transverse to the one or more lengths of the tubing received in the at least one tubing holder and configured to cut the one or more lengths of tubing upon moving; and
    a connector holder comprising:
        the at least one cutter at an edge thereof and adjacent to the at least one tubing holder, and
        a compartment housing a substantially sterile tubing connector, said connector holder being movable in relation to the tubing holder wherein the connector holder is moved to a position where the at least one cutter cuts the one or more lengths of tubing and the one or more lengths of tubing cut become aligned with the sterile tubing connector and urged together with the sterile tubing connector.

2. The apparatus of claim 1, further comprising a sterilant reservoir, adapted to supply the sterilant to the one or more sterilant applicators.

3. The apparatus of claim 2, wherein the sterilant reservoir comprises a breakable ampoule containing the sterilant.

4. The apparatus of claim 3, wherein the sterilant in the breakable ampoule is an aqueous solution comprising hydrogen peroxide.

5. The apparatus of claim 4, wherein the solution comprises 3 to 60 wt % hydrogen peroxide.

6. The apparatus of claim 5, wherein the solution comprises 25 to 35 wt % hydrogen peroxide.

7. The apparatus according to claim 1, further comprising a movable cover, which in a closed position delimits a cutting and connecting compartment and in an open position allows removal of the cut and connected one or more lengths of tubing.

8. The apparatus according to claim 1, wherein the tubing connector is a hose barb connector.

9. The apparatus according to claim 1, wherein the tubing connector comprises a port covered with a removable protective film or cap.

10. The apparatus of claim 1, wherein each of the at least one tubing holder is adapted to receive a respective one of the one or more lengths of tubing at a point distant from the ends of said one of the one or more lengths of tubing.

11. The apparatus according to claim 1, wherein the tubing connector is prepared from a deformable plastic and a central part of said tubing connector is concentrically contained in a notched metal tube adapted to upon external compression cut off the tubing connector and fluidically seal off ends of the tubing connector that are cut.

12. The apparatus according to claim 1, wherein one or more of the at least one cutter comprises a blade or a sharp edge of the connector holder.

13. The apparatus according to claim 1, which has been sterilized, using ionizing radiation.

14. The apparatus according to claim 1, wherein the at least one cutter and connector holder are rotationally or linearly movable in relation to the at least one tubing holder.

15. A method for a substantially sterile connection of flexible tubing in a non-heating process, comprising the steps of:
providing the apparatus of claim 1 and at least one length of flexible tubing;
placing the at least one length of tubing in the at least one tubing holder and applying sterilant to the at least one length of tubing with the one or more sterilant applicators;
moving the at least one cutter to cut the at least one length of tubing;
moving the connector holder to the position where the connector is aligned with the at least length of tubing that is cut;
urging the connector and the at least one length of tubing that is cut together to form a connected assembly; and
removing the connected assembly from the apparatus.

16. The method of claim 15, further comprising, before placing the at least one length of tubing in the at least one tubing holder and applying the sterilant to the at least one length of tubing with the one or more sterilant applicators, a step of fluidically connecting the sterilant in the sterilant reservoir with the one or more sterilant applicators.

17. The method of claim 16, further comprising a step of breaking an ampoule containing the sterilant.

18. The method of claim 15, wherein the at least one cutter and the connector holder are rotationally or linearly moved.

* * * * *